(12) United States Patent
Chang

(10) Patent No.: US 10,245,603 B2
(45) Date of Patent: Apr. 2, 2019

(54) VOLATILIZATION DEVICE CAPABLE OF AUTOMATIC QUANTITATIVE SUPPLEMENT OF LIQUID

(71) Applicant: Guangzhou Faner Aroma Product Co., Ltd., Guangzhou (CN)

(72) Inventor: Hsu-Hui Chang, Guangzhou (CN)

(73) Assignee: GUANGZHOU FANER AROMA PRODUCT CO., LTD., Guangzhou, Guangdong (CN)

(*) Notice: Subject to any disclaimer, the term of this patent is extended or adjusted under 35 U.S.C. 154(b) by 107 days.

(21) Appl. No.: 15/453,909

(22) Filed: Mar. 9, 2017

(65) Prior Publication Data

US 2018/0257095 A1    Sep. 13, 2018

(51) Int. Cl.
*A61L 9/03*    (2006.01)
*B01F 3/04*    (2006.01)
*B05B 7/28*    (2006.01)
*B05B 7/24*    (2006.01)

(52) U.S. Cl.
CPC ....... *B05B 7/28* (2013.01); *A61L 9/03* (2013.01); *B01F 3/04007* (2013.01); *B05B 7/2491* (2013.01)

(58) Field of Classification Search
CPC ........... B01F 3/04; B01F 3/04007; A61L 9/03

USPC ............. 261/26, 30, 72.1, DIG. 65; 422/124
See application file for complete search history.

(56) References Cited

U.S. PATENT DOCUMENTS

2004/0096369 A1* 5/2004 Daoting ............... A61L 2/20
                                                                422/124

* cited by examiner

*Primary Examiner* — Robert A Hopkins
(74) *Attorney, Agent, or Firm* — Leong C. Lei

(57) ABSTRACT

A volatilization device capable of automatic quantitative supplement of liquid includes: a vaporizer, defining an accommodation space and having an opening, air inlet and liquid inlet, the accommodation space being in communication with the opening, air inlet and liquid inlet; a gas supply, connected correspondingly to the gas inlet, allowing the gas supply to input gas to the vaporizer; and a liquid supply, having a liquid container, controller and press piece, the liquid container being connected to the controller and press piece, the controller being connected correspondingly with the liquid inlet, allowing the liquid supply to input liquid to the vaporizer, where the controller controls the start of the press piece to absorb the liquid in the liquid container, and input the liquid to the liquid inlet, and aerosol will be ejected from the opening when the liquid and gas is input to the accommodation space.

4 Claims, 7 Drawing Sheets

US 10,245,603 B2

VOLATILIZATION DEVICE CAPABLE OF AUTOMATIC QUANTITATIVE SUPPLEMENT OF LIQUID

(a) TECHNICAL FIELD OF THE INVENTION

The present invention relates to a volatilization device capable of automatic quantitative supplement of liquid, and more particularly to a volatilization device capable of automatic quantitative supplement of liquid, allowing the volatilization quantity of the liquid in a vaporizer to be controlled, and the liquid input in the volatilization device to be converted into aerosol spray in a scheduled time period.

(b) DESCRIPTION OF THE PRIOR ART

Referring to FIG. 7, which is a schematic view of a conventional vaporizer in which liquid is added manually, the liquid in a liquid container 301 is filled into a vaporizer 10 in a manual way when the liquid is wanted to add in the vaporizer 10, and the vaporizer 10 is then used to volatilize the liquid, which has the defects:
1. In conventional vaporizers, the volatilization quantity of liquid in the liquid container cannot be controlled, and the liquid is volatilized outward only through an air hole configured on the vaporizer.
2. In conventional vaporizers, the liquids have different viscosities because the liquids accommodated in the liquid container are different, resulting in different liquid volatilization speeds, and thus, they cannot be controlled.
3. In conventional vaporizers, the liquid remaining in the vaporizer cannot be recycled, resulting in waste.

SUMMARY OF THE INVENTION

The main object of the present invention is to provide a volatilization device capable of automatic quantitative supplement of liquid, capable of controlling the volatilization quantity of the liquid in a vaporizer, and converting the liquid input to the vaporizer into aerosol spray in a scheduled time period.

To achieve the object mentioned above, the present invention proposes a volatilization device capable of automatic quantitative supplement of liquid, including: a vaporizer, defining an accommodation space and having an opening, air inlet and liquid inlet, the accommodation space being in communication with the opening, air inlet and liquid inlet; a gas supply, in corresponding connection with the gas inlet, allowing the gas supply to input gas to the vaporizer; and a liquid supply, provided with a liquid container, controller and press piece, the liquid container being in connection with the controller and press piece, the controller being in corresponding connection with the liquid inlet, allowing the liquid supply to input liquid to the vaporizer, where the controller is adapted to control the start of the press piece to absorb the liquid in the liquid container and input the liquid to the liquid inlet, and aerosol will be ejected from the opening of the vaporizer when the liquid enters the accommodation space and the gas supply input gas to the accommodation space.

According to the volatilization device capable of automatic quantitative supplement of liquid mentioned above, the controller is adapted to control absorption quantity of the liquid in the liquid container, and input the liquid to the vaporizer from the liquid container.

According to the volatilization device capable of automatic quantitative supplement of liquid mentioned above, the vaporizer will convert the liquid input thereto into aerosol spray in a scheduled time period.

According to the volatilization device capable of automatic quantitative supplement of liquid mentioned above, the vaporizer is further configured with a reflux tube, one end thereof is in connection with the vaporizer and another end thereof the liquid container, too much the liquid input to the vaporizer from the liquid supply flows back to the liquid container through the reflux tube.

According to the volatilization device capable of automatic quantitative supplement of liquid mentioned above, the liquid in the liquid container is essence, deodorant pharmaceutical, sterilization agent, insect repellent or biotechnological preparation.

According to the volatilization device capable of automatic quantitative supplement of liquid mentioned above, the gas supply is an air press pump.

DETAILED DESCRIPTION OF THE PREFERRED EMBODIMENTS

Figure 1:
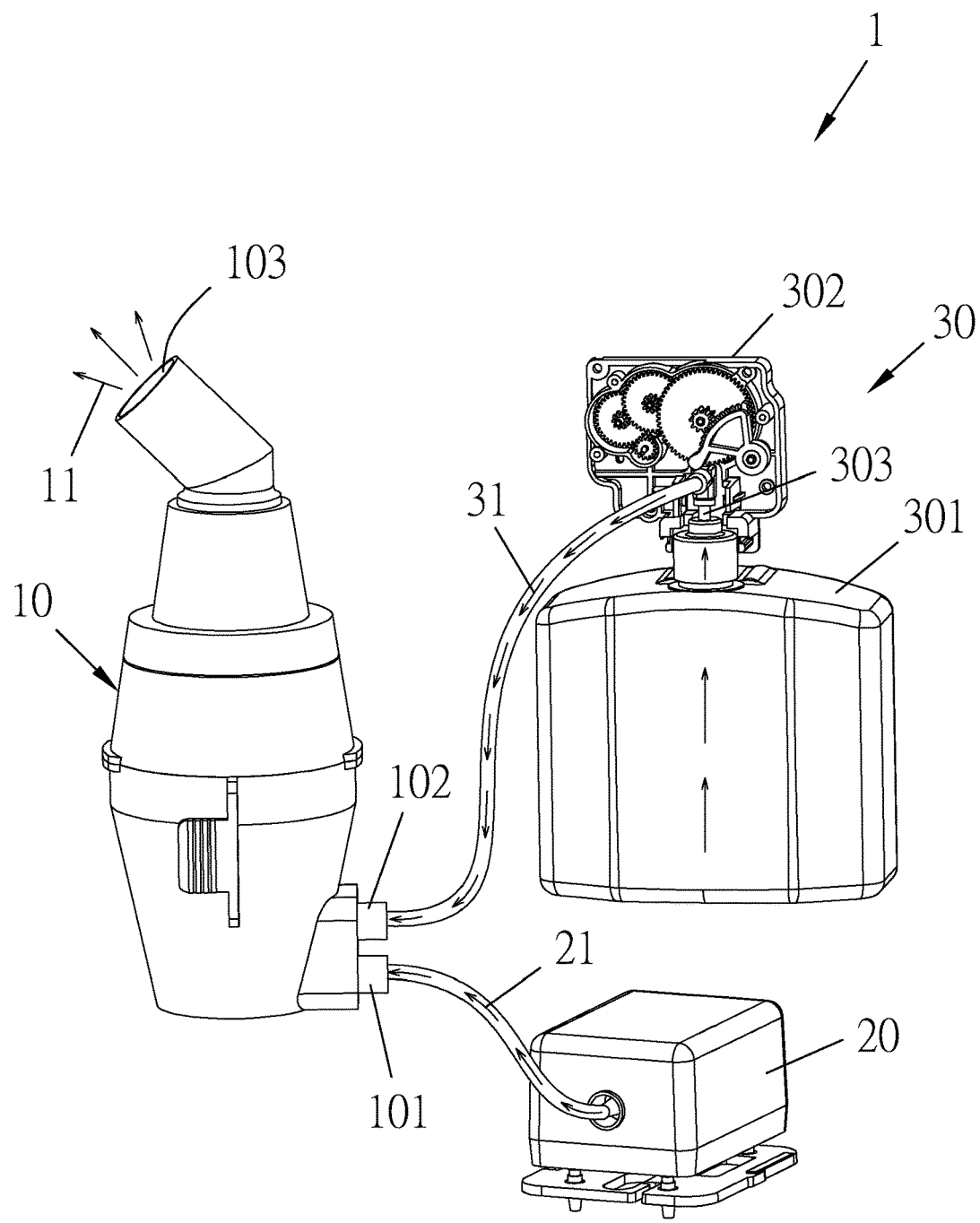
FIG. 1 is a schematically perspective view of a first preferred embodiment view of the present view.
Figure 2:
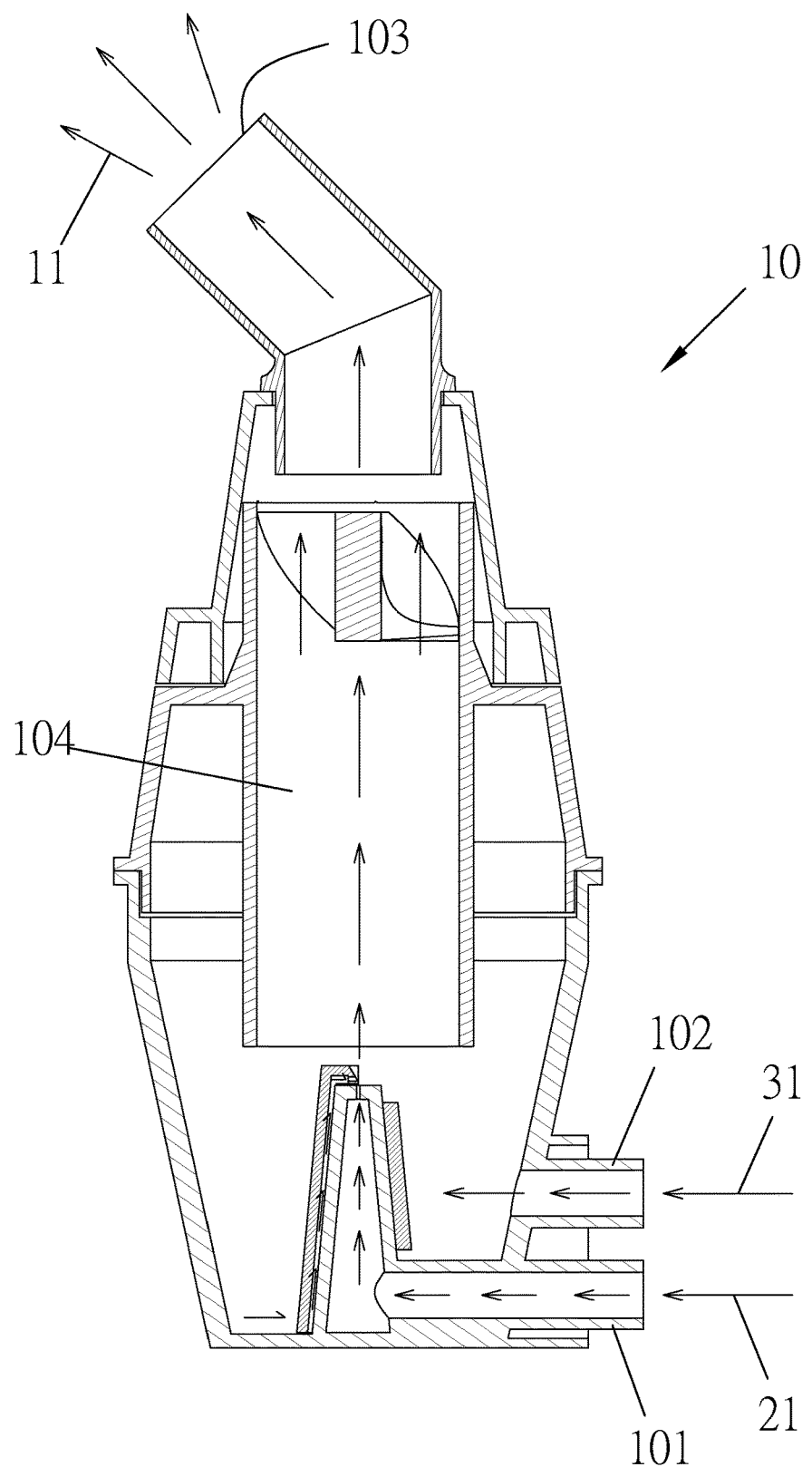
FIG. 2 is a cross-sectional view of a vaporizer of the first embodiment of the present invention.
Figure 3:
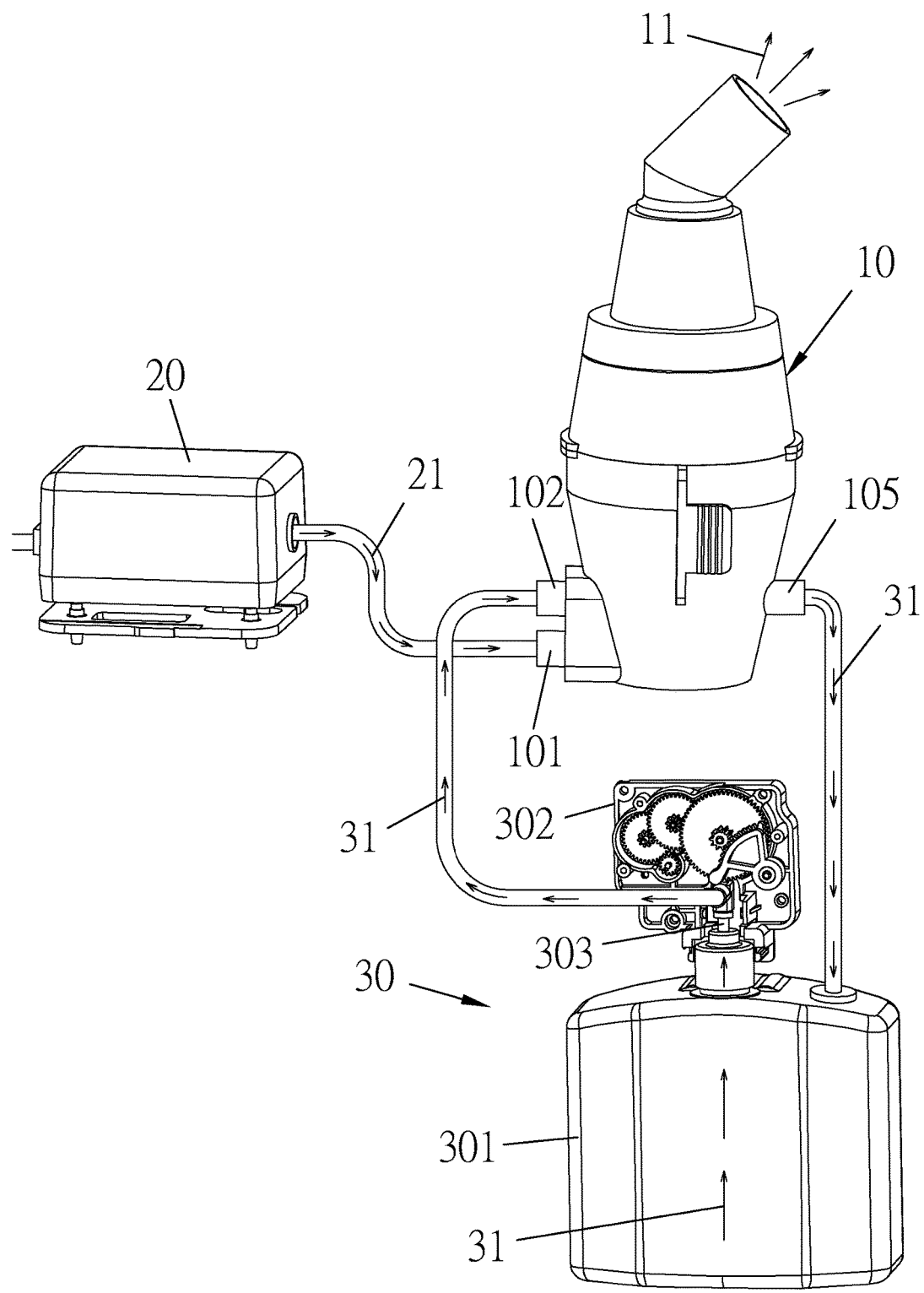
FIG. 3 is a schematically perspective view of a second preferred embodiment of the present invention.
Figure 4:
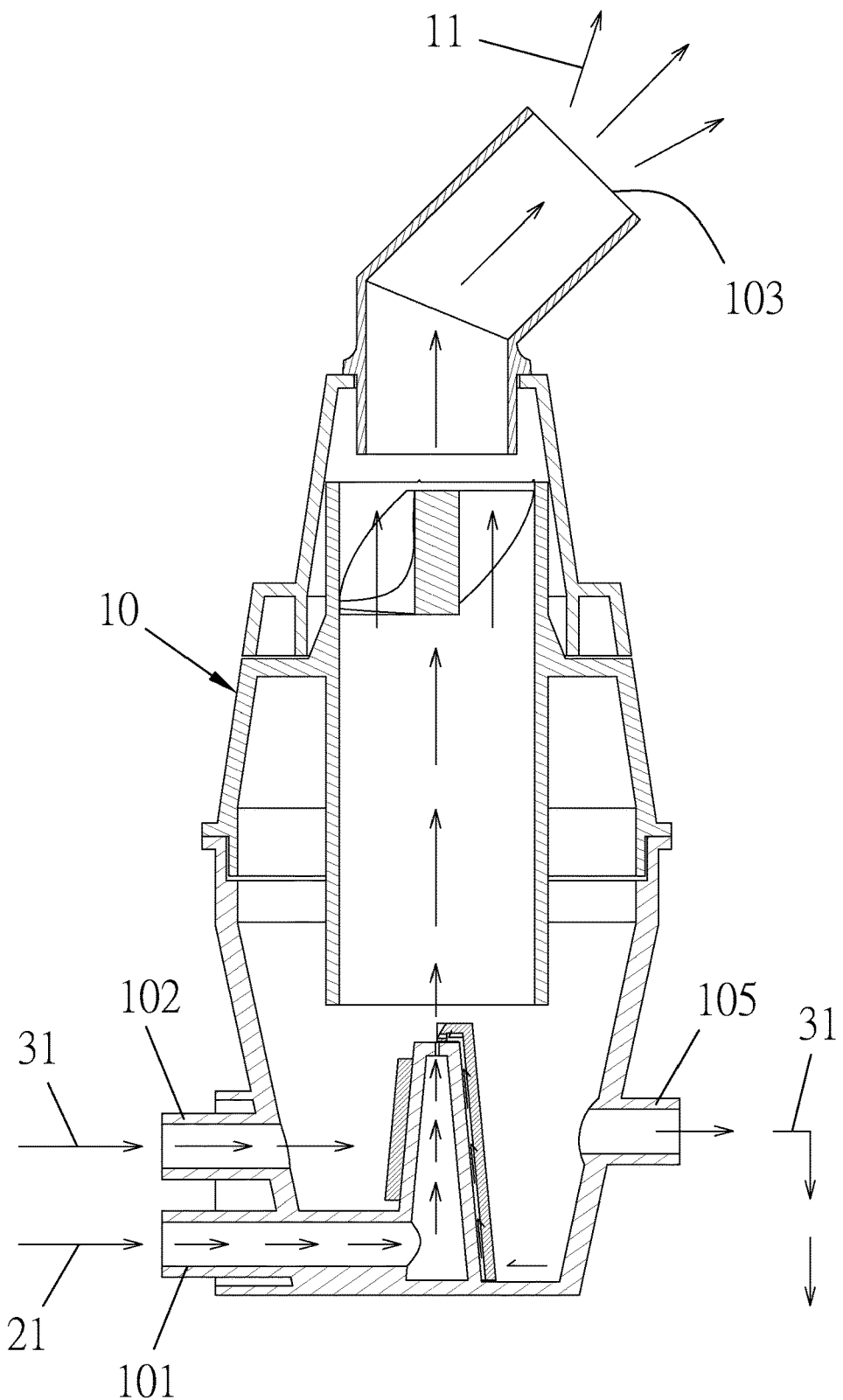
FIG. 4 is a cross-sectional view of a vaporizer of the second embodiment of the present invention.
Figure 5:
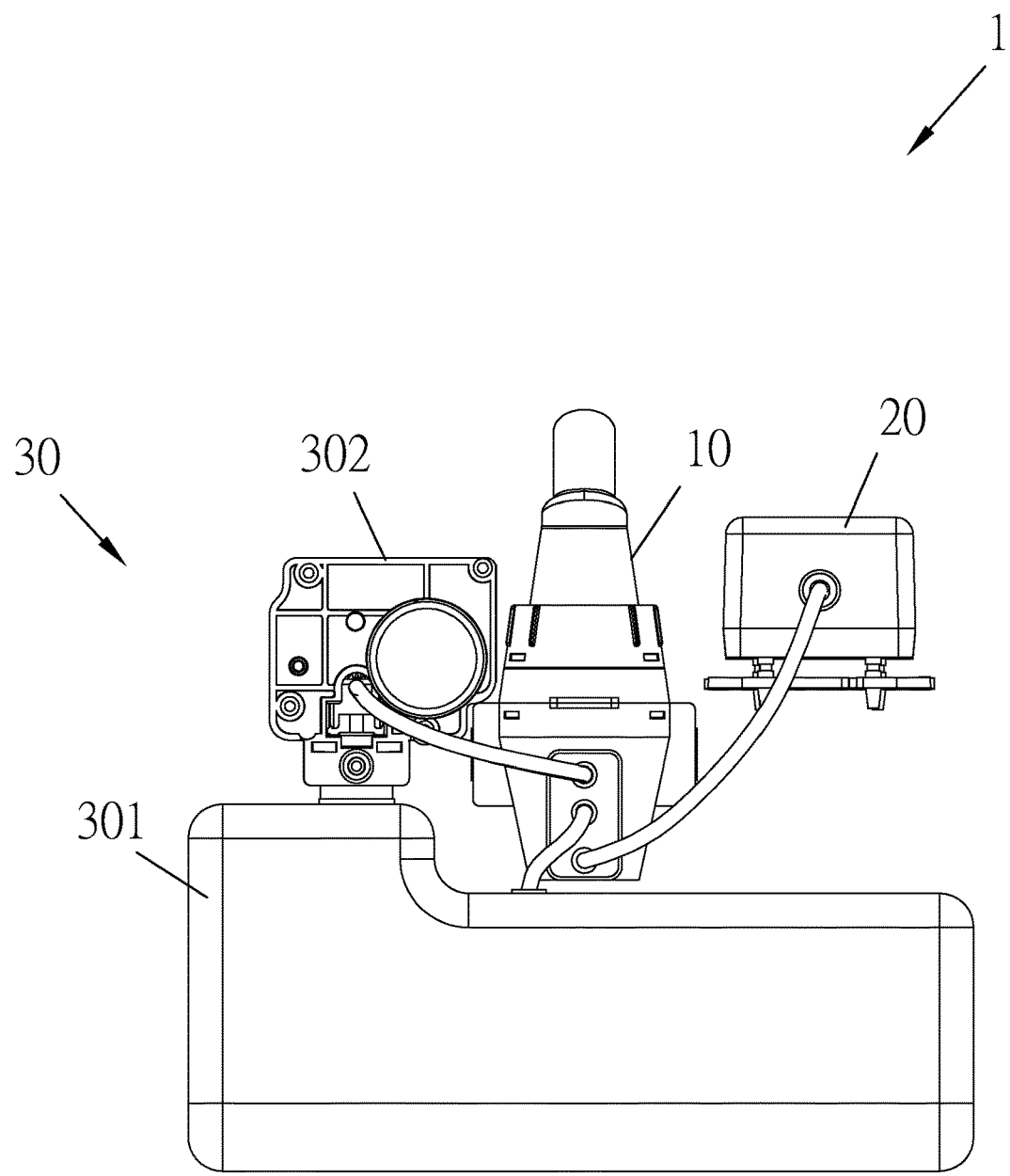
FIG. 5 is a schematic view of the structure of the second embodiment of the present invention.
Figure 6:
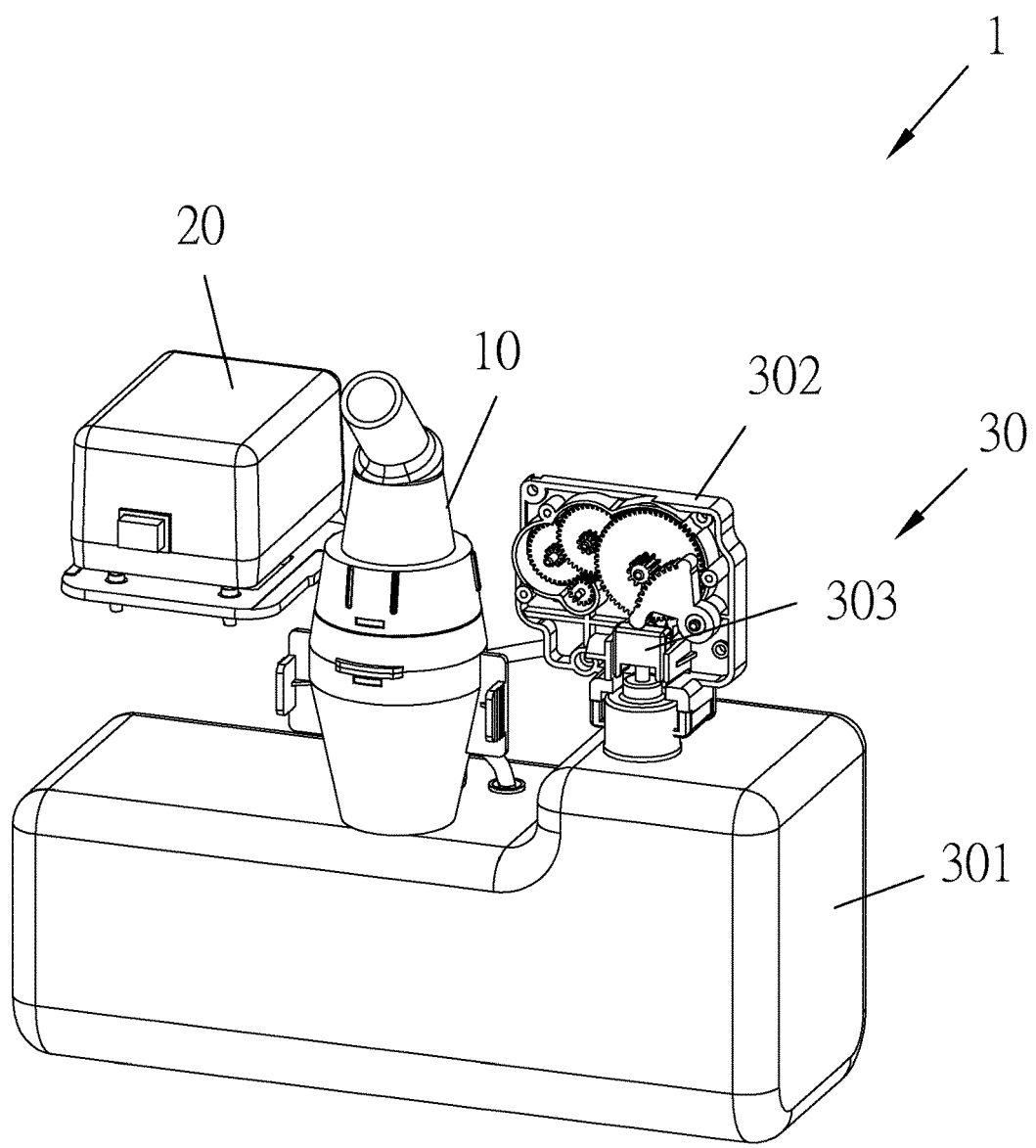
FIG. 6 is a schematically perspective view of the structure of the second embodiment of the present invention.
Figure 7:
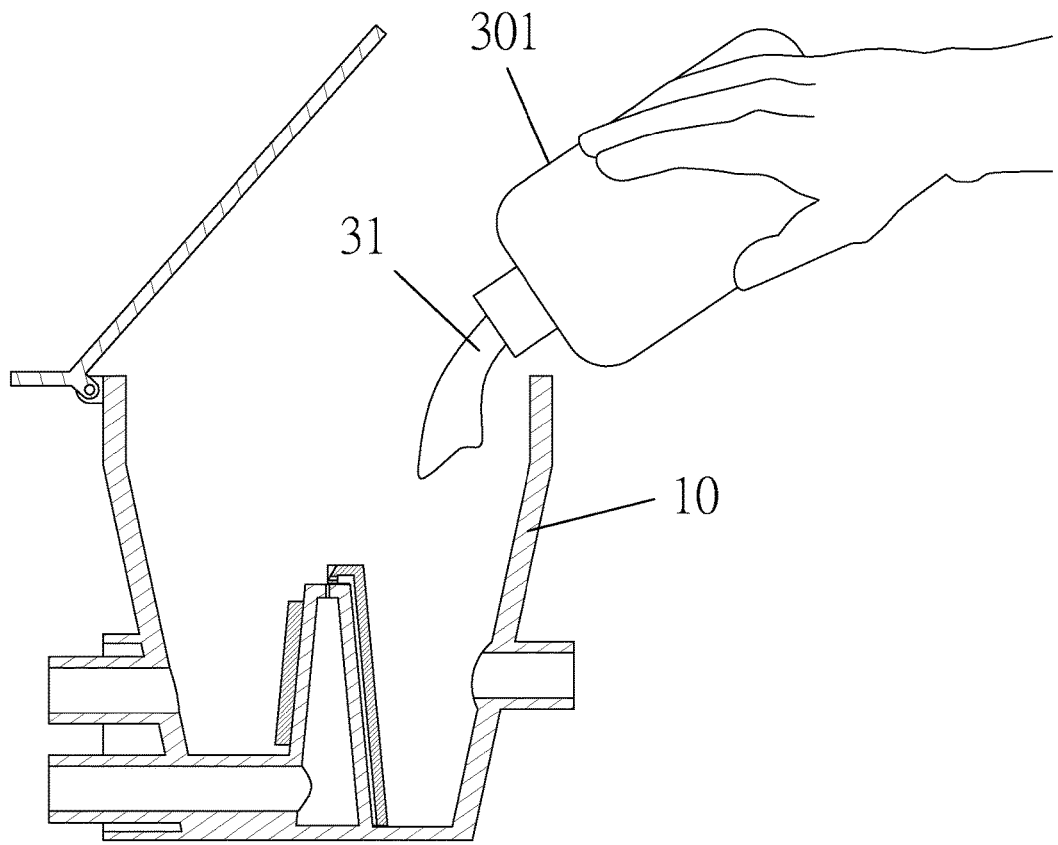
FIG. 7 is a schematic view of a conventional vaporizer, where liquid is added therein in a manual way.

Referring to FIGS. 1 and 2, which respectively show a first preferred embodiment of the present invention, a volatilization device 1 capable of automatic quantitative supplement of liquid according to the present invention includes a vaporizer 10 defining an accommodation space 104 and having an opening 103, gas inlet 101 and liquid inlet 102, where the accommodation space 104 is in communication with the opening 103, gas inlet 101 and liquid inlet 102. Furthermore, a gas supply 20 is in corresponding connection with the gas inlet 101, allowing the gas supply 20 to input gas 21 into the vaporizer 10, and a liquid supply 30 has a liquid container 301, controller 302 and press piece 303, where the liquid container 301 is in connection with the controller 302 and press piece 303, and the controller 302 is in corresponding connection with the gas inlet 102, allowing the liquid supply 30 to input liquid 31 to the vaporizer 10, where the controller 302 is adapted to control the start of the press piece 303 to absorb the liquid 31 inside the liquid container 301, and input the liquid 31 to the liquid inlet 102. When the liquid 31 enters the accommodation space 104 and the gas supply 20 inputs the gas into the accommodation space 104, aerosol 11 will be ejected from the opening 103 of the vaporizer 10.

Particularly, the gas supply 20 is an air compressor pump, and the vaporizer 10, according to Venturi Principle, inputs the compressed gas 21 to the gas inlet 101 with the gas supply 20, and the liquid 31 will be drawn out to become the aerosol 11 through the fast flow of the gas 21, allowing the vaporizer 10 to eject the aerosol 11.

Furthermore, the controller 302 is used to control the absorption quantity of the liquid in the liquid container 301 and input the liquid 31 of the liquid container 301 to the vaporizer 10, and the vaporizer 10 will convert the liquid 31 input to the vaporizer 10 to the aerosol 11 and then eject it Referring to FIGS. 3 to 6, which respectively show a second preferred embodiment of the present invention, a volatilization device 1 capable of automatic quantitative supplement of liquid includes a vaporizer 10 defining an accommodation space 104 and having an opening 103, gas inlet 101, liquid inlet 102 and reflux tube 105, where the accommodation space 104 is in communication with the opening 103, gas inlet 101 and liquid inlet 102.

Furthermore, a gas supply 20 is in corresponding connection with the gas inlet 101, allowing the gas supply 20 to input gas 21 to the vaporizer 10, and a liquid supply 30 has a liquid container 301, controller 302 and press piece 303, where the liquid container 301 is in connection with the controller 302 and press piece 303, and the controller 302 is in corresponding connection with the gas inlet 102, allowing the liquid supply 30 to input liquid 31 to the vaporizer 10. Furthermore, the liquid container 301 is in connection with the reflux tube 105; too much liquid 31 input to the vaporizer 10 from the liquid supply 30 will flow back the liquid container 301 through the reflux tube 105. In addition, the controller 302 is adapted to control the start of the press piece 303 to absorb the liquid 31 inside the liquid container 301, and input the liquid 31 to the liquid inlet 102. When the liquid 31 enters the accommodation space 104 and the gas supply 20 inputs the gas into the accommodation space 104, aerosol 11 will be ejected from the opening 103 of the vaporizer 10.

Furthermore, the liquid 31 in the liquid container 301 is essence, deodorant pharmaceutical, sterilization agent, insect repellent or biotechnological preparation. If the liquid 31 in the liquid container 301 is essence, the essence can be converted into aerosol spray, making air fresh; if the liquid 31 in the liquid container 301 is deodorant pharmaceutical, the deodorant pharmaceutical can be converted into aerosol spray, capable of inhibiting stink; if the liquid 31 in the liquid container 301 is sterilization agent, the sterilization agent is converted into aerosol spray, capable of air sterilization; if the liquid 31 in the liquid container 301 is insect repellant, the insect repellant is converted into aerosol spray, achieving an inset repelling effect; and if the liquid 31 in the liquid container 301 is biotechnological preparation, the biotechnological preparation is converted into aerosol spray, capable of pest control.

I claim:

1. A volatilization device capable of automatic quantitative supplement of liquid, comprising:
    a vaporizer, defining an accommodation space and having an opening, an air inlet and a liquid inlet, said accommodation space being in communication with said opening, said air inlet and said liquid inlet;
    a gas supply, in corresponding connection with said gas inlet, allowing said gas supply to input gas to said vaporizer so as to generate a gas flow in the accommodation space of said vaporizer; and
    a liquid supply, provided with a liquid container, a controller and a press piece, said liquid container being in connection with said controller and said press piece, said controller being in corresponding connection with said liquid inlet, allowing said liquid supply to input liquid to the accommodation space of said vaporizer,
    wherein said controller is operable to control the press piece to withdraw said liquid from said liquid container to the accommodation space of said liquid inlet, wherein the liquid is converted into aerosol with the gas flow generated in the accommodation space and the aerosol is ejected outward from said opening of said vaporizer; and
    wherein said vaporizer comprises a reflux tube, which has an end in connection with the accommodation space of said vaporizer and an opposite end connected to said liquid container, such that an excessive amount of said liquid accumulated in the accommodation space of said vaporizer is conducted from said vaporizer back to said liquid container through said reflux tube.

2. The device according to claim 1, wherein said controller is operable to control a quantity of said liquid withdrawn from said liquid container, and input the quantity of said liquid to said vaporizer from said liquid container.

3. The device according to claim 1, wherein said liquid in said liquid container is one of essence, deodorant pharmaceutical, sterilization agent, insect repellent and biotechnological preparation.

4. The device according to claim 1, wherein said gas supply is an air compressor pump.

* * * * *